United States Patent
Pop

(10) Patent No.: US 12,339,222 B1
(45) Date of Patent: Jun. 24, 2025

(54) WELLBORE FLUID OPTICAL SPECTRA EXTRACTION

(71) Applicant: Schlumberger Technology Corporation, Sugar Land, TX (US)

(72) Inventor: Julian J. Pop, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/760,948

(22) Filed: Jul. 1, 2024

(51) Int. Cl.
- *G01N 33/28* (2006.01)
- *E21B 49/10* (2006.01)
- *G01N 21/3577* (2014.01)
- *G01N 21/85* (2006.01)

(52) U.S. Cl.
CPC ......... *G01N 21/3577* (2013.01); *E21B 49/10* (2013.01); *G01N 21/85* (2013.01); *G01N 33/2823* (2013.01)

(58) Field of Classification Search
CPC .............. G01N 21/3577; G01N 21/85; G01N 33/2823; G01N 21/31; E21B 49/10; E21B 49/08; E21B 49/0875
See application file for complete search history.

(56) References Cited

U.S. PATENT DOCUMENTS

| | | |
|---|---|---|
| 6,992,768 B2 | 1/2006 | Dong |
| 7,178,591 B2 | 2/2007 | Del Campo |
| 7,703,517 B2 | 4/2010 | Tarvin |
| 7,857,049 B2 | 12/2010 | Sherwood |
| 11,635,369 B1 * | 4/2023 | Swett ................. G01N 21/3577 356/51 |
| 2008/0173445 A1 * | 7/2008 | Dong ................... E21B 49/087 166/264 |
| 2015/0308261 A1 * | 10/2015 | Zuo ........................ E21B 49/08 166/250.01 |

OTHER PUBLICATIONS

Smits et al., "In-Situ Optical Fluid Analysis as an Aid to Wireline Formation Sampling", SPE Formation Evaluation, SPE-26496, Jun. 1, 1995, pp. 91-98.

Indo et al., "Estimation of Fluid Composition from Downhole Optical Spectrometry", Society of Petroleum Engineers, SPE-166464, 30 Sep. 2013, 21 pages.

* cited by examiner

*Primary Examiner* — David P Porta
*Assistant Examiner* — Mamadou Faye
(74) *Attorney, Agent, or Firm* — Jeffrey D. Frantz

(57) ABSTRACT

A method for evaluating a formation fluid includes flowing formation fluid through a flowline in a downhole fluid sampling and evaluation measurement tool deployed in a wellbore and making optical absorption measurements on the flowing formation fluid to generate a plurality of optical density spectra. A spectrum from the plurality of generated spectra is selected using predetermined selection criteria that are based on optical density values at one or more selected wavelengths in the generated spectra. At least one fluid property is estimated from the selected spectrum.

13 Claims, 8 Drawing Sheets

WELLBORE FLUID OPTICAL SPECTRA EXTRACTION

CROSS REFERENCE TO RELATED APPLICATIONS

None.

BACKGROUND

Subterranean wells are commonly drilled to explore and recover natural hydrocarbon deposits located in the Earth's crust. During a drilling operation, formation fluids are commonly sampled and evaluated to obtain information about a reservoir's fluid composition and gas-oil ratio (GOR) as well as other properties of the fluid. This information may be used for field planning decisions and for the optimization of upstream and downstream production facilities.

Formation fluid samples are commonly obtained using both logging while drilling (LWD) tools deployed in the drill string and wireline tools that are run into the well after the well (or a segment thereof) has been drilled. LWD tools may be employed to obtain and analyze samples during non-drilling intervals, for example, when a new stand or joint is added to the drill string. One example of an LWD fluid sampling and analyzing evaluation tool is the SpectraSphere fluid mapping while drilling tool (available from SLB). The Modular Formation Dynamics Tester (also available from SLB) is an example wireline fluid sampling and analyzing evaluation tool.

One difficulty with analyzing the sampled formation fluid is that the presence of water in the sampled fluid (e.g., originating in the formation itself or from water-based drilling fluid) can significantly affect the estimated fluid gas-oil ratio (GOR). Dewatering algorithms have been developed to mitigate these effects, however, the presence of water in the fluid remains problematic, particularly for LWD based measurements. There is need in the industry for improved methods for analyzing sampled formation fluids.

BRIEF DESCRIPTION OF THE DRAWINGS

For a more complete understanding of the disclosed subject matter, and advantages thereof, reference is now made to the following descriptions taken in conjunction with the accompanying drawings, in which.

DETAILED DESCRIPTION

Downhole tools and methods for sampling and evaluating a composition of a formation fluid is disclosed. One example method includes flowing formation fluid through a flowline in a downhole fluid sampling and evaluation measurement tool deployed in a wellbore and making optical absorption measurements on the flowing formation fluid to generate a plurality of optical density spectra. A spectrum from the plurality of generated spectra is selected using predetermined selection criteria that are based on optical density values at one or more selected wavelengths in the generated spectra. At least one fluid property is estimated from the selected spectrum.

Figure 1:
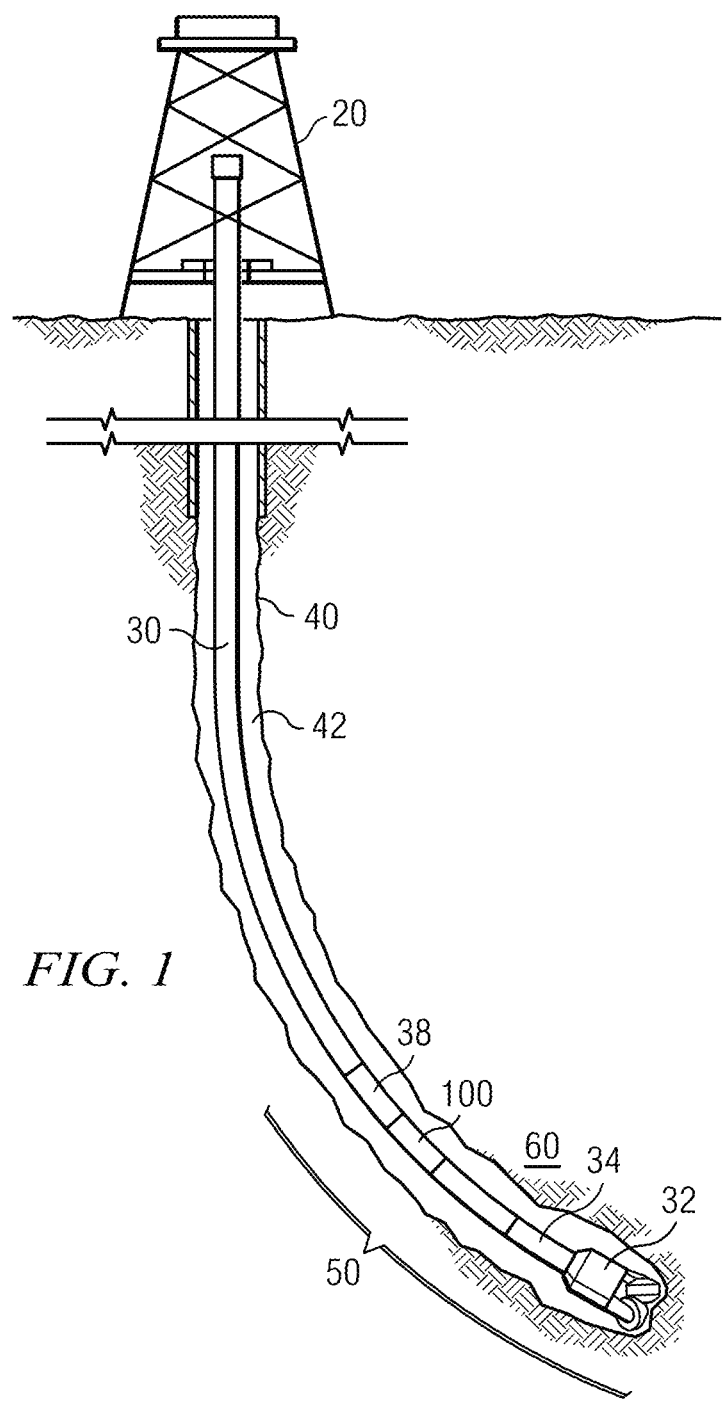
FIG. 1 depicts an example drilling rig including a disclosed downhole fluid sampling and evaluation measurement tool.

FIG. 1 depicts a schematic drilling rig 20 including a drill string 30 and a bottom hole assembly 50 deployed in the string disposed within a wellbore 40. The drilling rig 20 may be deployed in either onshore or offshore applications (an onshore application is depicted). Moreover, the wellbore may be inclined at substantially any angle and may include vertical, horizontal, and building sections (only vertical and building sections are depicted). The disclosed embodiments are not limited to any particular wellbore configuration. In the depicted example, the wellbore 40 may be formed in subsurface formations by rotary drilling in a manner that is well-known to those or ordinary skill in the art (e.g., via well-known directional drilling techniques).

As is known to those of ordinary skill, the drill string 30 may be rotated, for example, at the surface to drill the well (e.g., via a rotary table or via a hydraulically powered motor deployed in or above the BHA 50). A pump may deliver drilling fluid through the interior of the drill string 30 to the drill bit 32 where it exits the string via ports therein. The fluid may then circulate upwardly through the annular region 42 between the outside of the drill string 30 and the wall of the wellbore 40. In this known manner, the drilling fluid lubricates the drill bit 32 and carries formation cuttings up to the surface.

In the illustrated example embodiment, the BHA 50 may include any number of downhole tools, for example, including a steering tool 34 and a measurement while drilling (MWD) tool 38. As depicted the BHA further includes an LWD fluid sampling and evaluation measurement tool 100. As described in more detail below, measurement tool 100 may be configured to obtain a formation fluid sample and to analyze the sample to estimate a composition of the formation fluid. The BHA may further optionally include other LWD tools, one or more stabilizers, as well as other tools such as a reamer. The disclosed embodiments are not limited to any particular BHA configuration.

Figure 2:
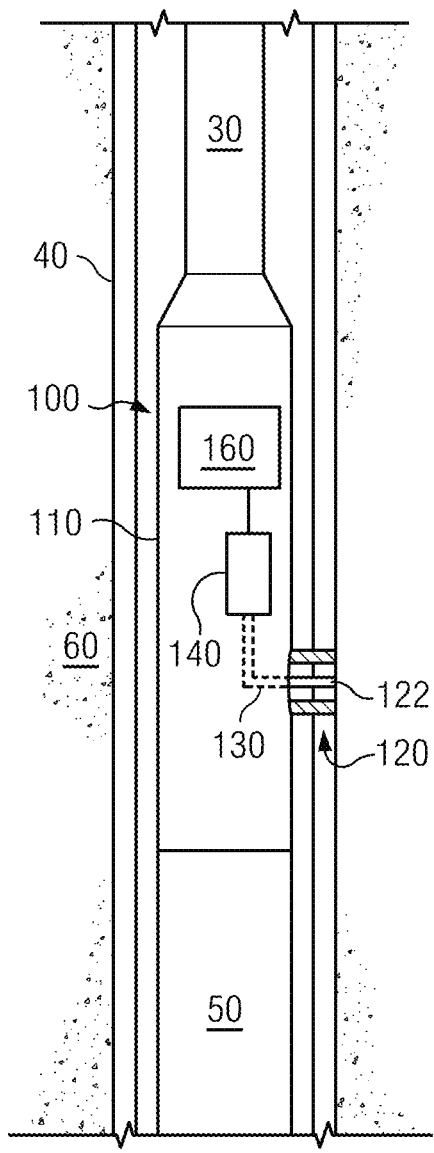
FIG. 2 schematically depicts the downhole fluid sampling and evaluation measurement tool shown on FIG. 1.

Turning now to FIG. 2, one example embodiment of a fluid sampling and evaluation measurement tool 100 is depicted in a wellbore (e.g., as shown in FIG. 1). Measurement tool 100 may include a downhole tool body 110 such as an LWD tool body configured for deployment in (and coupling with) a BHA in a drill string. For example, the tool body may include threaded ends (not shown) for coupling with the drill string and may be configured to withstand the harsh drilling environment including severe shocks and vibrations. The measurement tool 100 may further include a probe 120 configured to sealingly engage a wellbore wall and to pump or draw wellbore fluid into the tool via an input port 122. The input port 122 is in fluid communication with an internal flowline 130 and at least one optical measurement assembly 140 that is configured to make optical absorption measurements of the wellbore fluid. A controller 160 may be configured to operate the measurement tool 100 as well as evaluate and interpret optical measurements made using the optical measurement assembly 140 as described in more detail below. While the example embodiment depicted on FIG. 2 does not depict a sampling pump, it will be appreciated that a sampling pump may be deployed along flowline 130 or above assembly 140 such that it draws the fluid through the assembly 140. The disclosed embodiments are, of course, not limited in this regard.

The controller 160 may be further configured to execute the disclosed methods (e.g., methods 200 and 250 described in more detail below with respect to FIGS. 5 and 6). It will, of course, be appreciated that the controller may include computer hardware and software configured to cause the measurement tool to make the optical measurements (for example to cause the optical measurement assembly to make optical measurements during a non-drilling interval) as well as to automatically execute one or more of the disclosed methods. The hardware may include one or more processors (e.g., microprocessors) which may be connected to one or more data storage devices (e.g., hard drives or solid state memory) and user interfaces. It will be further understood that the disclosed embodiments may include processor executable instructions stored in the data storage device. The disclosed embodiments are, of course, not limited to the use of or the configuration of any particular computer hardware and/or software.

Figure 3:
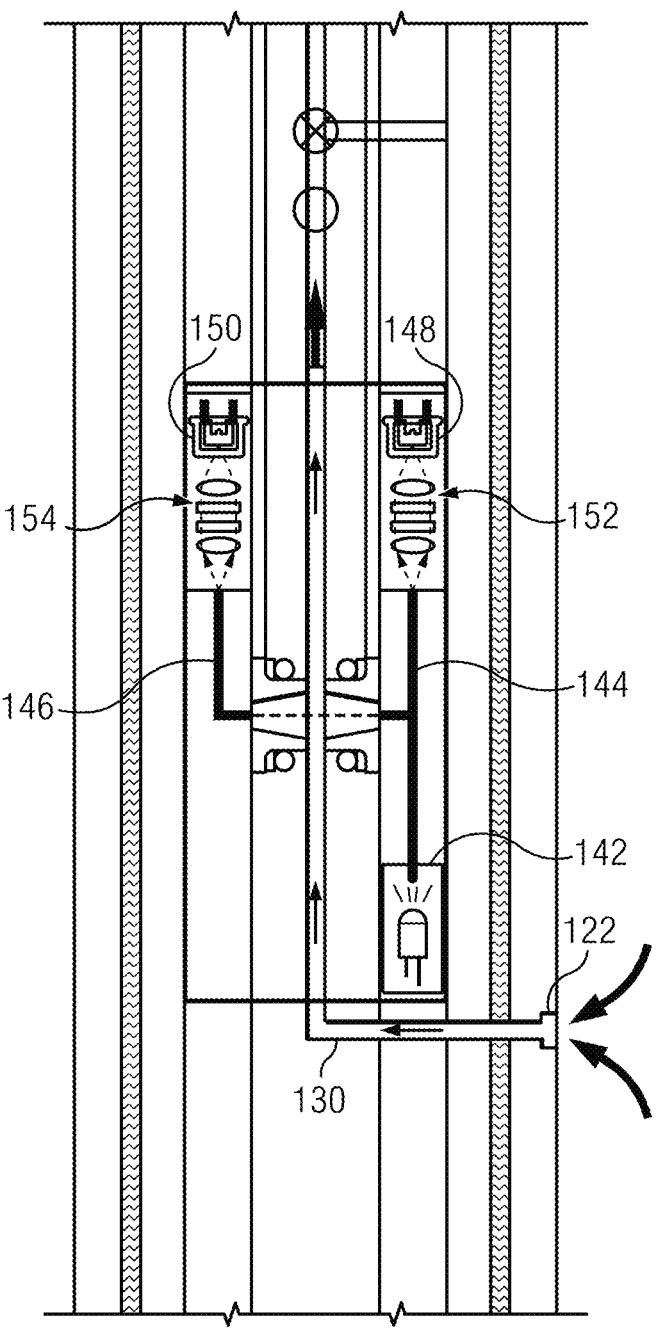
FIG. 3 depicts a portion of the downhole fluid sampling and evaluation measurement tool shown on FIG. 2.

Turning now to FIG. 3, a portion of downhole measurement tool 100 is schematically depicted. As described above with respect to FIG. 2, measurement tool 100 includes a probe having an input port 122 in fluid communication with an internal flowline 130. In example embodiments, the optical measurement assembly 140 may include a light source 142, a reference signal path 144 and a sample or measurement signal path 146. The light source 142 may include, for example, a halogen lamp, a light-emitting diode, a laser, or any other suitable optical source. The reference signal path 144 may include an optical fiber that couples the light source 142 with a first detector 148 and the sample or measurement signal path 146 may include an optical fiber that couples the light source 142 with a second detector 150. Each of the signal paths 144, 146 may further include a corresponding lens and bandpass filter arrangement 152, 154 configured to focus and filter light emanating from the light source such that the light received by the spectrometers 148, 150 is within a particular frequency band. In example embodiments, optical absorption measurements may be made at a predetermined number of discrete optical wavelengths in the visible and near infrared (e.g., 20 discrete wavelengths in a band ranging from about 400 nm to about 2100 nm).

With continued reference to FIG. 3, the detectors 148, 150 are in electronic communication with the controller 160. In operation, the light source 142 emits light that traverses both the reference signal path 144 and the measurement signal path 146. As depicted, the light traversing the measurement signal path 146 passes through a transparent portion of the flow line 130 and the corresponding formation fluid within the flowline 130. The controller may be configured to generate an optical density spectrum from the detector measurements made at each of the detectors 148, 150. Moreover, the controller may be configured to cause the measurement tool 100 to make the optical measurements at substantially any suitable time interval, for example, at a frequency in a range from about 1 to about 10 Hz. The disclosed embodiments are of course not limited in this regard.

Figure 4:
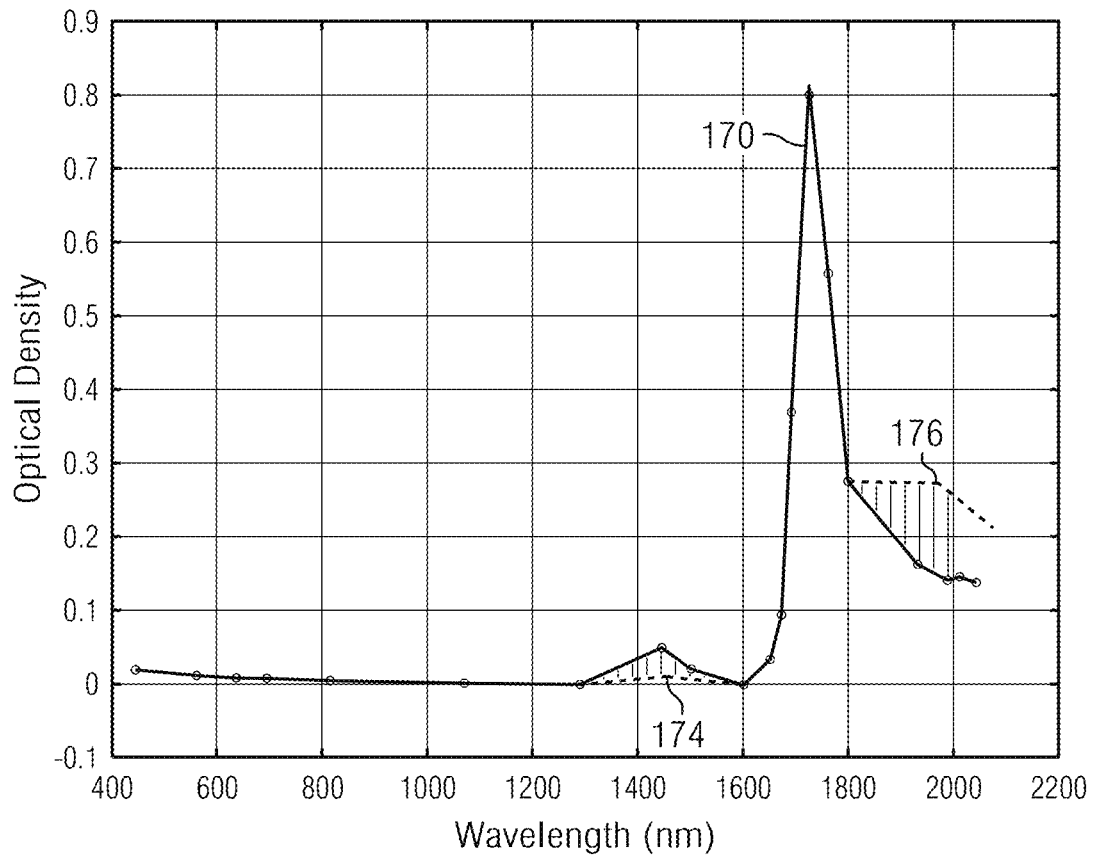
FIG. 4 depicts one example optical density spectrum (a plot of the measured optical density versus the wavelength of the incident light) for a example hydrocarbon sample.

FIG. 4 depicts one example optical density spectrum for an example heptane oil sample. The spectrum is a plot of the measured optical density versus the wavelength of the incident light, baseline shifted to have an optical density of zero at 1600 nm. In this spectrum, the optical density is the negative base 10 logarithm of the ratio of the optical intensity measured at the measurement spectrometer 150 to the optical intensity measured at the reference spectrometer 148. Moreover, in this example spectrum the optical density is measured at 20 discrete optical wavelengths as indicated by the open circles in the plot. An absorption peak is observed at about 1700 nm as indicated at 170. As described above, the presence of water in the sampled fluid (e.g., originating in the formation itself or from water-based drilling fluid) can significantly influence (or distort) the measured absorption spectra. The influence of even very small amounts of water (e.g., less than a few percent) is often observed particularly at wavelengths between about 1300 and 1600 nm as indicated by the dashed line at 174 and more significantly between about 1800 and 2100 nm as indicated by the dashed line at 176. Such spectral distortion can significantly impact the estimated composition of the hydrocarbon sample as well as the estimated GOR.

Currently available measurement methods make use of a dewatering algorithm that subtracts a scaled reference water spectrum from the measured spectrum. The reference water spectrum may be scaled, for example, by an estimated water volume fraction (WATF) of the sample. While this approach has been and continues to be commercially serviceable (and may be intuitively appealing), there is room for further improvement. In particular, determining an appropriate scaling factor can be difficult as the estimated WATF often lacks precision (e.g., can have large error bands). Moreover, the reference water spectrum is not always representative of an actual water spectrum in the wellbore environment in which the water temperature and/or salinity may not match those used in a laboratory environment.

One aspect of the disclosed embodiments was the realization that it may be possible to identify a spectrum (or even multiple spectra) from among the large number of measured spectra in a sampling operation that are representative of the unadulterated formation fluid (e.g., not contaminated with water). In particular, it was realized that there may exist regions in the flow field such that the entire beam of incident light may pass only through one type of fluid, either hydrocarbon or water, and that the corresponding measured spectra at that instant (time) may be representative of a pure hydrocarbon (e.g., pure oil) or pure water measurement. It was further realized that fluid flow conditions through the probe and flowline may be selected or tailored to promote "slug" flow in which the fluid phases are separated in such a way that the incident light may only pass through a single phase in the flowline. Moreover, it was still further realized that since oil and water are generally immiscible and that their respective physical properties are not generally modified by the presence of the other that such representative spectra may accurately portray the optical properties of the pure oil or pure water components.

Figure 5:
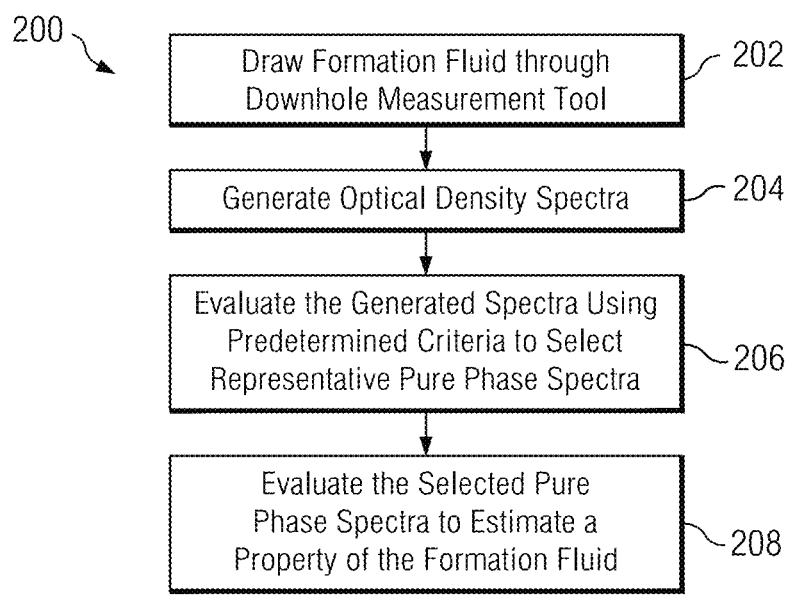
FIG. 5 depicts a flowchart of one example method for estimating a composition of a formation fluid.

Turning now to FIG. 5, a flowchart of one example method 200 for making optical density measurements of a formation fluid is depicted. The method includes receiving (e.g., flowing) a formation fluid through a flowline in a downhole fluid sampling and evaluation measurement tool at 202. The measurement tool may be deployed in a drill string, for example, as described above with respect to FIGS. 1-3, although the disclosed embodiments are expressly not limited in this regard. A plurality (e.g., a large number) of optical density spectra are generated at 204 while flowing the fluid through the flowline in 202 (e.g., at a predetermined time interval or frequency). Generating the spectra may include, for example, making optical absorption measurements. The generated spectra are evaluated according to predetermined criteria at 206 to select at least one spectrum from among the generated spectra that is representative of a pure phase fluid. For example, the spectrum (or spectra) selected at 206 may be representative of a pure oil phase measurement, a pure gas phase measurement, or a pure water phase measurement. The selection criteria are based on optical density values at one or more selected wavelengths in the generated spectra criteria, for example, comparing measured optical density(ies) at one (or more) wavelength(s) to measured optical density (ies) measured at one (or more) other wavelength(s) or to values computed by mathematically combining the measured optical density(ies) measured at the one (or more) other wavelength(s) in the spectra. In embodiments in which the selected spectrum is representative of an oil or gas fluid, the selected spectrum may then be further evaluated to estimate at least one property of the fluid, such as the composition, the GOR, or the formation-volume-factor (FVF), of the oil sample at 208, amongst other properties. Such other properties may include, but are not limited to, mass density, compressibility, saturation pressure, and asphaltene content.

Figure 6:
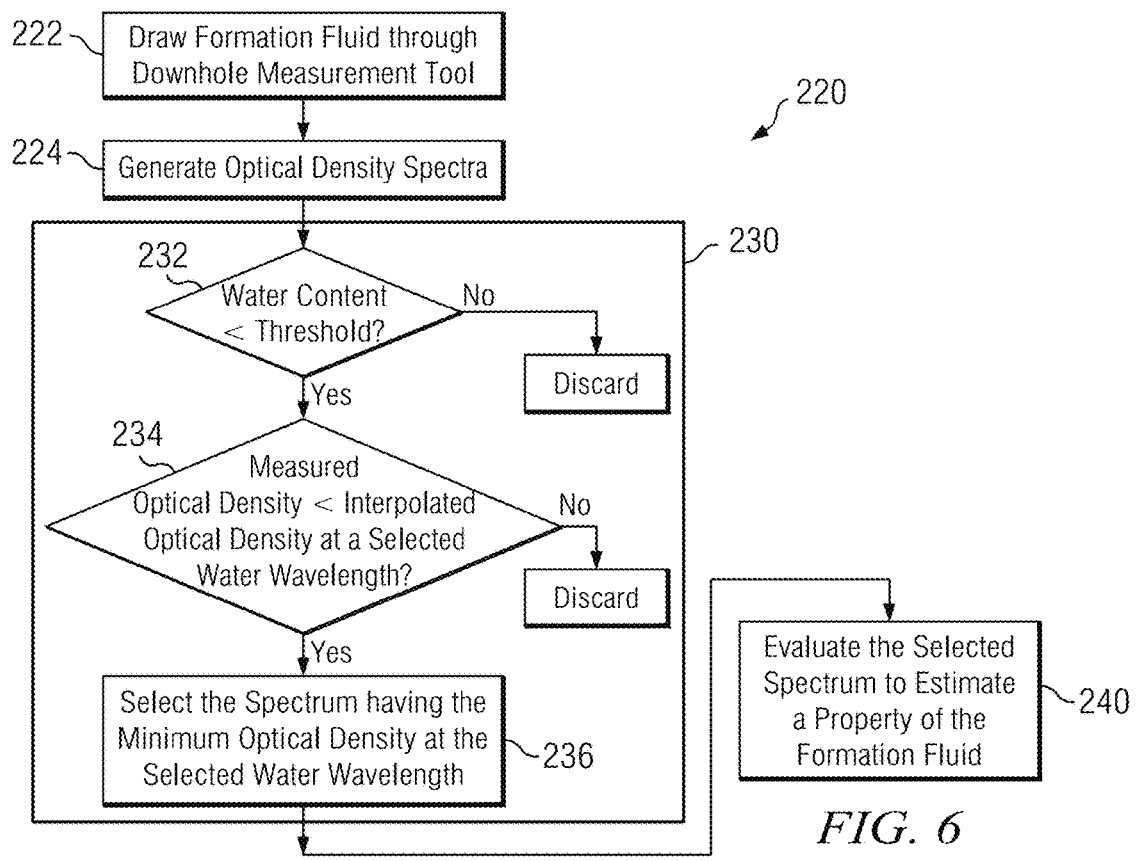
FIG. 6 depicts a flowchart of another example method for estimating a composition of a formation fluid.

FIG. 6 depicts a flowchart of another example method 220 for making optical density measurements of a formation fluid. Method 220 is similar to method 200 in that optical density spectra are generated at 224 while flowing a formation fluid through a flowline in a fluid sampling and evaluation measurement tool at 222. In this example, the spectra are evaluated according to a series of criteria at 230 to select the best spectrum from among the set of generated spectra. In particular, in this example embodiment, the criteria at 230 are selected to identify the best hydrocarbon (e.g., gas or oil) spectrum among the set of generated spectra.

In a first criterion 232, spectra with a WATF (water fraction) greater than a threshold are discarded (and spectra with a WATF less than or equal to the threshold are retained for further evaluation). This first criterion is intended to eliminate spectra for which the sample is known to have appreciable water. For example, the threshold may be 5 volume percent water (e.g., 2 volume percent or even 1 volume percent). Moreover, in some example embodiments the threshold may be 0 volume percent water such that the spectra are discarded when WATF>0 or stated another way in some example embodiments spectra are only selected for further evaluation when the estimated WATF=0. The WATF may be estimated from the measured spectra, for example, using the procedure disclosed in Smits, et al., SPE 26496, 1995 in which the water fraction is represented by $f_w$.

The second criterion 234 compares a measured optical density with an interpolated estimate of the optical density at a wavelength in a region in the spectra that is known to be influenced by water contamination. In example embodiments, this region of the spectra may have a wavelength that is greater than the wavelength of the primary oil peak in the generated spectra. For example only, the measured optical density and the interpolated estimate of the optical density may make use of optical density measurements at first, second, and third wavelengths that are greater than or equal to 1800 nm when the primary oil peak is observed at 1725 nm. In this second criterion, spectra are discarded when the measured optical density at the selected wavelength is greater than or equal to the estimated optical density obtained by interpolation (or selected for further evaluation when the measured optical density is less than the estimated optical density obtained by interpolation).

The third criterion 236 selects a single spectrum from among those selected using the second criterion 234. The selected spectrum has the lowest optical density at the selected wavelength. In other words, the spectrum that has the lowest optical density at the selected wavelength is selected as the best hydrocarbon (e.g., oil) spectrum from among the set of generated spectra at 234. This single selected spectrum may then be further evaluated to estimate at least one property of the oil sample, e.g., the composition or the GOR, using techniques known to those of ordinary skill.

With continued reference to FIG. 6, the above described criteria are now described in more detail. These criteria may be represented using the following mathematical notation in which $\Omega(t, \lambda)$ represents the optical density (absorbance) measured at wavelength $\lambda$ and time t. Moreover, an estimated optical density at a selected wavelength $\lambda 2$ may be obtained by linear interpolation using the measured optical densities at first and third wavelengths $\lambda 1, \lambda 3$ on either side of the selected wavelength and may be given as follows:

$$\Omega(t, \lambda 1, \lambda 2, \lambda 3)_{INT} \equiv \Omega(t, \lambda 2)_{EST} = \Omega(t, \lambda 1) + \frac{\Omega(t, \lambda 3) - \Omega(t, \lambda 1)}{\lambda 3 - \lambda 1}(\lambda 2 - \lambda 1) \tag{1}$$

Note that in Eq. (1) both the selected wavelength $\lambda 2$ and the wavelengths used for the interpolation $\lambda 1, \lambda 3$ may be defined as part of the selection criteria. As also indicated in Eq. (1), the linear interpolation may be thought of as the estimated optical density value at the second wavelength on a straight line connecting the measured optical densities at the first and third wavelengths. The linear interpolation is represented herein as follows: $\Omega(t, \lambda 1, \lambda 2, \lambda 3)_{INT}$. In one example embodiment, the second criterion 234 may be represented as follows, when the first, second, and third wavelengths are 1800 nm, 1930 nm, and 1985 nm:

$$\Omega(t, 1930)_{MEAS} < \Omega(t, 1800, 1930, 1985)_{INT} \tag{2}$$

It will be appreciated that Eq. (2) indicates that the criterion is satisfied when the measured optical density at 1930 nm is less than the estimated optical density at 1930 nm obtained by linear interpolation of the measured optical densities at 1800 nm and 1985 nm. The disclosed embodiments are, of course, not limited in this regard. In example embodiments 1800 nm<$\lambda 2$<2000 nm.

With continued reference to FIG. 6, it will be appreciated that the second criterion 234 may be modified (or expanded or restated) such that the measured optical density at the second wavelength is less than an estimated optical density at the second wavelength (obtained by interpolation) within threshold limits, for example, as follows:

$$\Omega(t,\lambda2)_{MEAS} < \Omega(t,\lambda1,\lambda2,\lambda3)_{INT} + \epsilon_1 \quad (3)$$

$$\Omega(t,\lambda2)_{MEAS} < \Omega(t,\lambda1,\lambda2,\lambda3)_{INT} - \epsilon_2 \quad (4)$$

Where, for example, $\epsilon_2 \sim 10\epsilon_1$ and $0.001 < \epsilon_1 < 0.01$ in optical density units. In such embodiments, the first equation including the $+\epsilon_1$ term may allow for measurement noise and the second equation including the $-\epsilon_2$ term may ensure that the optical density at the second wavelength is not unrealistically low.

In further example embodiments the evaluation at 234 may include the use of other selection criteria. For example, additional criteria may be used to ensure that the selected spectra include acceptable oil absorption peaks. Such additional criteria may include one or more of the following:

$$\Omega(t,1725)_{MEAS} > \Omega(t,1760)_{MEAS} \quad (5)$$

$$\Omega(t,1800)_{MEAS} > \Omega(t,1985)_{MEAS} \quad (6)$$

$$\Omega(t,1800)_{MEAS} < (\Omega(t,1760)_{MEAS} + \Omega(t,1985)_{MEAS})/\alpha \quad (7)$$

where $\alpha$, for example, has a value $1.5 < \alpha < 3$.

Such criteria may be intended to ensure that a significant oil absorption peak is measured and is centered at about 1725 nm (e.g., rather than 1760 nm) and that the shape or width of the peak is consistent with a characteristic oil peak.

In still other example embodiments the selection criteria at 234 may include evaluating the spectra for the presence of a minor peak at a wavelength less than the major oil peak. The minor peak may be observed at a wavelength between 1300 nm and 1600 nm, for example at a wavelength of about 1450 nm (e.g., 1445 nm). This additional criterion may evaluate the measured optical densities at first, second, and third wavelengths that are less than the wavelength of the primary oil peak in the generated spectra. For example only, the first, second, and third wavelengths may each be less than or equal to 1600 nm when the primary oil peak is observed at 1725 nm. According to this additional and optional criterion, spectra may be selected when the measured optical density at the second (selected) wavelength is greater than an interpolated estimate of the optical density at the second wavelength (thereby indicating the presence of the minor peak). In one example embodiment, this additional criterion may be expressed as follows:

$$\Omega(t,1445)_{MEAS} > \Omega(t,1290,1445,1600)_{INT} \quad (8)$$

when the minor peak is centered at about 1445 nm.

With still further reference to FIG. 6, it will be appreciated that criteria 232, 234, and 236 are intended to select a single representative spectrum from among all of the measured spectra. The first criterion may select a first subset of spectra for which WATF<Threshold (e.g., WATF=0). The second criterion may select a second (smaller) subset of spectra from among the first subset for which $\Omega(t, \lambda2)_{MEAS} < \Omega(t, \lambda1, \lambda2, \lambda3)_{INT}$. As noted above other criteria may also be applied when selecting the second subset. The third criterion may then select the single spectrum from among the second subset of spectra for which the optical density at the second wavelength (e.g., 1930 nm) is minimized, for example, after subtracting a background optical density as follows:

$$\min_t \{\Omega(t, \lambda2)_{MEAS} - \Omega(t, 1600)_{MEAS}\} \quad (9)$$

It will be appreciated that when identifying the spectrum with the minimum optical density at a given wavelength, that the spectra being evaluated may be advantageously normalized, for example, via removing the background. In example embodiments in which hydrocarbon spectra are being evaluated, the normalization may include shifting the spectra such that the optical density is zero at 1600 nm (e.g., as shown in Eq. (9)). In example embodiments in which water spectra are being evaluated, the normalization may include shifting the spectra such that the optical density is zero at 1070 nm. The disclosed embodiments are, of course, not limited in these regards.

It will be appreciated that the selection criteria may be applied to a large set or number of generated spectra or alternatively may be applied spectrum by spectrum as each spectrum is generated during the fluid logging operation. For example, the generated spectra may be stored in a memory buffer and then processed after the spectra have been acquired to obtain the above described first and second subsets and the selected spectrum. In an alternative embodiment that may be advantageous for downhole tools having limited electronic memory, each generated spectrum may be evaluated as it is acquired using the first criterion. When a newly acquired spectrum satisfies the first criterion it may then be evaluated using the second criterion. When the spectrum satisfies the second criterion it may then be compared with the previous best spectrum using the third criterion. In this way only the best spectrum is retained and all other spectra may be discarded (thereby reducing memory requirements).

Figure 7:
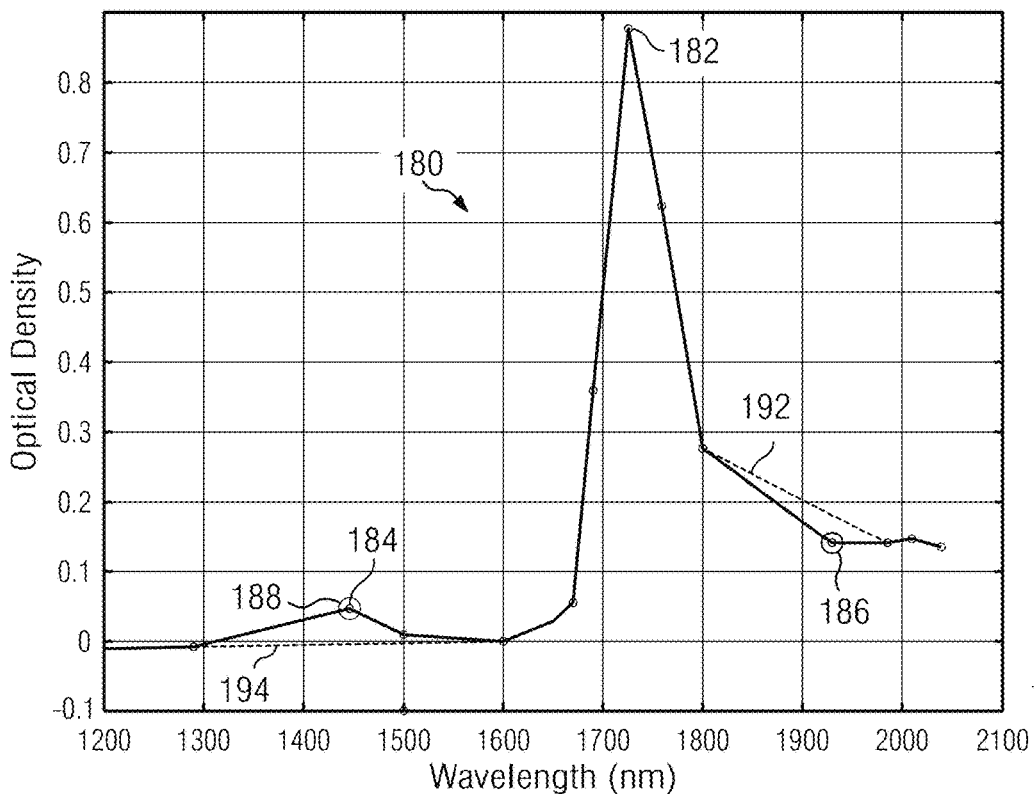
FIG. 7 depicts a portion of an optical density spectrum illustrating two example selection criteria for selecting a hydrocarbon spectrum.

Turning now to FIG. 7, a portion of an optical density spectrum 180 is depicted illustrating two example criteria (namely those given in Eqs. (2) and (8) above). In this example spectrum, a major oil peak is observed at 1725 nm as indicated at 182. A minor peak is observed at 1445 nm as indicated at 184. The optical density measurements at 1930 nm and 1445 nm are indicated at 186 and 188. In this example spectrum, the optical density measurement at 1930 nm 186 is less than the straight line 192 (the linear interpolation) connecting the optical densities measured at 1800 nm and 1985 nm indicating that the spectrum satisfies the criterion of Eq. (2). Moreover, the optical density measurement at 1445 nm is greater than the straight line 194 (the linear interpolation) connecting the optical densities measured at 1290 nm and 1600 nm. Again, the depicted spectrum satisfies the criterion of Eq. (8).

While the disclosed embodiments have been described above and exemplified with respect to selecting a best oil spectrum, it will be appreciated that methods 200 and 220 (FIGS. 5 and 6) are not so limited. In particular, method 200 may also be utilized to select or extract the best spectrum for a gas or a retrograde gas (a gas condensate). Moreover, method 200 may still further be utilized to select or extract a best spectrum for water. In method 200, the spectra generated at 204 are evaluated according to predetermined criteria to select at least one spectrum from among the generated spectra. It will be appreciated that the selection criteria for selecting a pure gas spectrum, a pure gas condensate spectrum, or a pure water spectrum may differ from those described above for selecting a pure oil spectrum.

Figure 8:
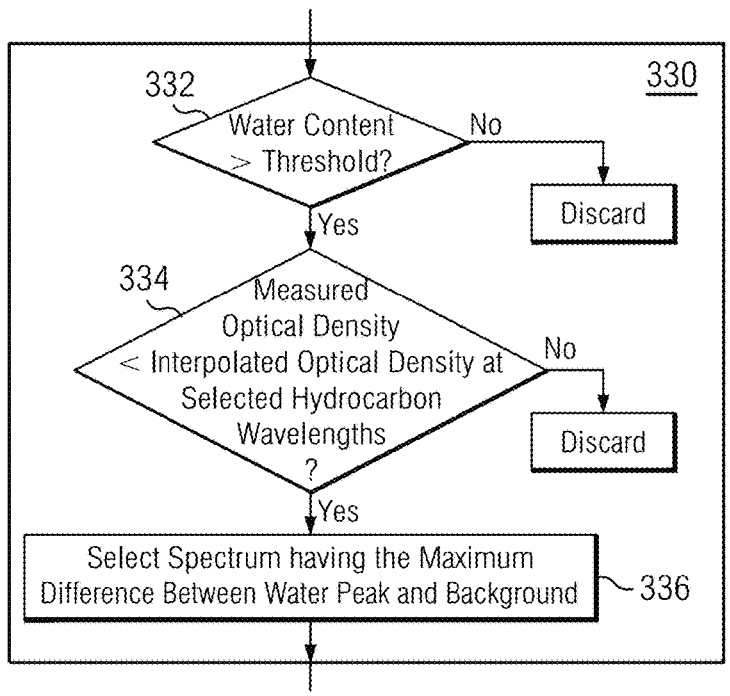
FIG. 8 depicts a flow chart of example selection criteria for selecting a water spectrum.

FIG. 8 depicts a flow chart of example selection criteria 330 for selecting a pure water spectrum. In a first criterion 332, spectra with a WATF less than a threshold are discarded (and spectra with a WATF greater than the threshold are retained for further evaluation). In example embodiments the threshold indicates a pure or nearly pure water spectrum. For example, the threshold may be 80 volume percent water (e.g., 90 volume percent water or 95 volume percent water). In a second criterion 334, spectra with a hydrocarbon peak (or alternatively an oil) peak less than a threshold (or below an interpolated background) may be retained for further evaluation while spectra with a hydrocarbon or oil peak greater than the threshold (or background) are discarded. A third criterion 336 may then select the best spectrum from the spectra remaining from 334 for which the water peak has a maximum optical density.

In one example embodiment, the first criterion 332 selects spectra for which WATF>0.95. In the second criterion 334, the measured optical densities at one or more (or even all) of the hydrocarbon peaks at 1671 nm, 1690 nm, and 1725 nm are less than estimated background optical densities obtained via linear interpolation. In example embodiments for which a hydrocarbon peak is less than the interpolated background, the criterion may be represented mathematically, for example, as follows:

$$\Omega(t,1671)_{MEAS}<\Omega(t,1600,1671,1800)_{INT} \quad (10)$$

$$\Omega(t,1690)_{MEAS}<\Omega(t,1600,1690,1800)_{INT} \quad (11)$$

$$\Omega(t,1725)_{MEAS}<\Omega(t,1600,1725,1800)_{INT} \quad (12)$$

In some example embodiments (e.g., in which there is some a-priori knowledge about the fluid composition) the second criterion 334 may be configured to evaluate only the oil peak against a threshold or background value. In one example embodiment this may be represented mathematically, for example, as follows:

$$\Omega(t,1690)_{MEAS}<\Omega(t,1671,1690,1760)_{INT} \quad (13)$$

$$\Omega(t,1725)_{MEAS}<\Omega(t,1671,1725,1760)_{INT} \quad (14)$$

The third criterion 336 may then select the best spectrum from the remaining spectra having a maximum difference between the optical density of the water peak and a background optical density. This third criterion may be represented mathematically, for example, as follows:

$$\max_t\{\Omega(t,1445)_{MEAS} - \Omega(t,1070)_{MEAS}\} \quad (15)$$

Figure 9:
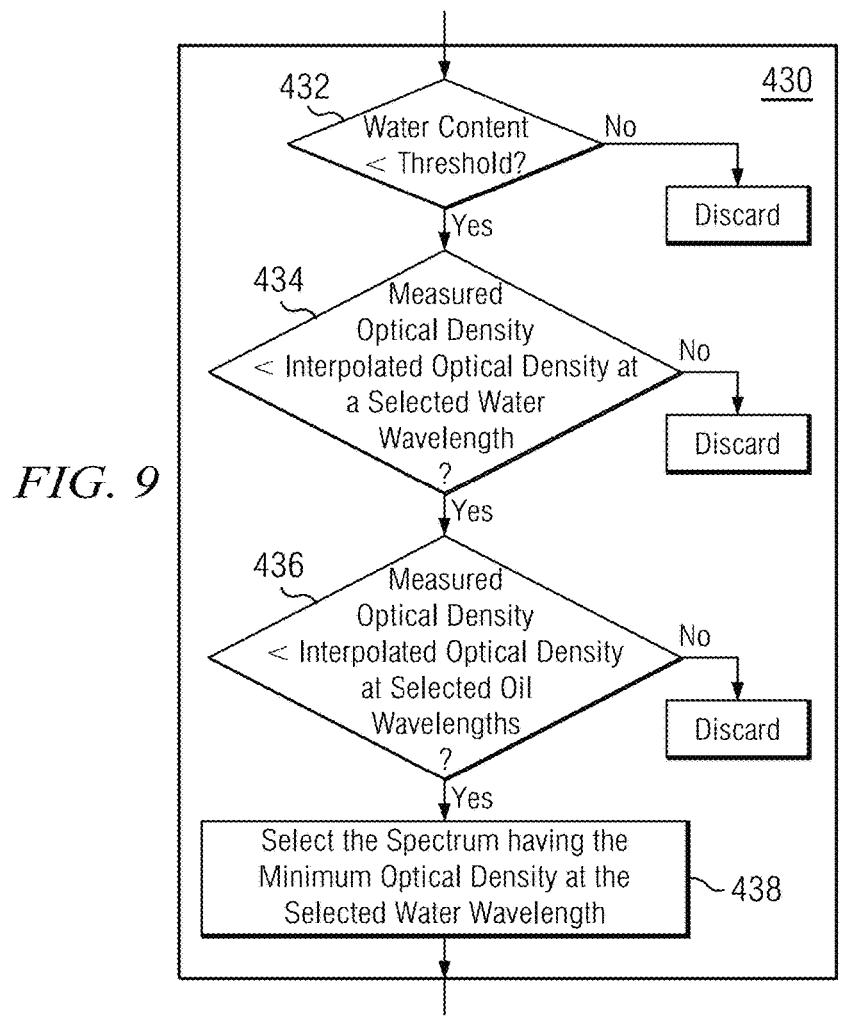
FIG. 9 depicts a flow chart of example selection criteria for selecting a gas spectrum.

FIG. 9 depicts a flow chart of example selection criteria 430 for selecting a gas spectrum. In a first criterion 432, spectra with a WATF greater than a threshold are discarded (and spectra with a WATF less than or equal to the threshold are retained or further evaluated). In example embodiments the threshold indicates a pure or nearly pure hydrocarbon spectrum. For example, the threshold may be 5 volume percent water (e.g., 2 volume percent water, 1 volume percent water, or even 0 volume percent water).

A second criterion 434 is similar to (or identical to) criterion 234 (FIG. 6) in that it evaluates the optical densities at first, second, and third wavelengths that are greater than a wavelength of a primary hydrocarbon peak in the generated spectra. Spectra are selected for further evaluation only when the measured optical density at the selected (second) wavelength is less than an interpolated estimate of the optical density at the selected wavelength as described above, for example, with respect to Eqs. (2)-(4).

A third criterion 436 may select spectra for which the measured optical density of an oil peak is less than the optical density of the local background (or of the shoulder of the gas peak). For example, the measured optical density at one or more wavelengths corresponding to the oil peak (or shoulders thereof) may be compared with linearly interpolated estimated optical densities at those wavelengths and the spectrum may be selected when the measured optical density (ies) are less than the estimated optical density (ies). In example embodiments, the third criterion may be expressed mathematically, for example, as follows:

$$\Omega(t,1690)_{MEAS}<\Omega(t,1671,1690,1800)_{INT} \quad (16)$$

$$\Omega(t,1725)_{MEAS}<\Omega(t,1671,1725,1800)_{INT} \quad (17)$$

$$\Omega(t,1760)_{MEAS}<\Omega(t,1671,1760,1800)_{INT} \quad (18)$$

A fourth criterion 438 may then select the spectrum from the remaining spectra which exhibits the smallest optical density difference at a distinguished water wavelength in a range from about 1800 nm to about 2000 nm (e.g., 1930 nm). This may be expressed mathematically, for example, as follows:

$$\min_t\{\Omega(t,1930)_{MEAS} - \Omega(t,1600)_{MEAS}\} \quad (19)$$

Figure 10:
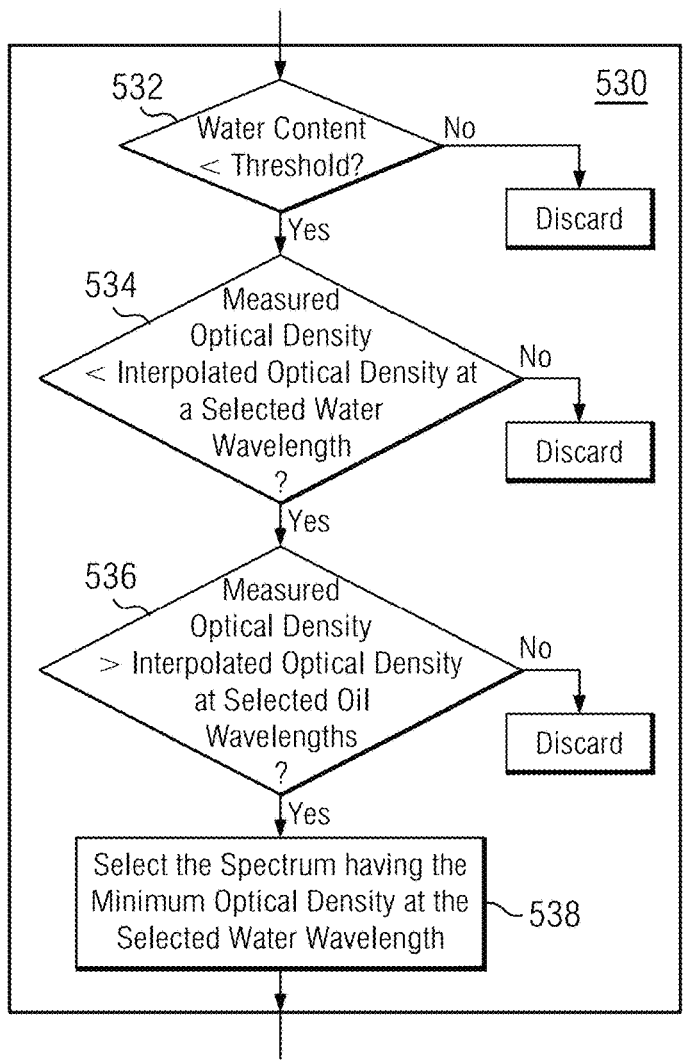
FIG. 10 depicts a flow chart of example selection criteria for selecting a gas condensate spectrum.

Turning now to FIG. 10 a flow chart of example selection criteria 530 for selecting a gas condensate spectrum is depicted. First and second criteria 532 and 534 may be substantially identical to criteria 432 and 434 (FIG. 9) described above for obtaining a gas spectrum. A third criterion 536 may recognize that the gas condensate peak is often similarly shaped to a combination of gas and oil peaks. Therefore, the third criterion may select spectra for which the measured optical density of an oil peak is greater than the optical density of the local background (e.g., linearly interpolated estimated optical densities or of the shoulder or background). In one embodiment, this may be expressed mathematically, for example, as follows:

$$\Omega(t,1690)_{MEAS}\geq\Omega(t,1671,1690,1800)_{INT} \quad (20)$$

$$\Omega(t,1725)_{MEAS}\geq\Omega(t,1671,1725,1800)_{INT} \quad (21)$$

$$\Omega(t,1760)_{MEAS}\geq\Omega(t,1671,1760,1800)_{INT} \quad (22)$$

A fourth criterion 538 may then select the spectrum from the remaining spectra which exhibits the smallest optical density at a distinguished water wavelength (e.g., 1930 nm) as given, for example, in Eq. (19).

Figure 11:
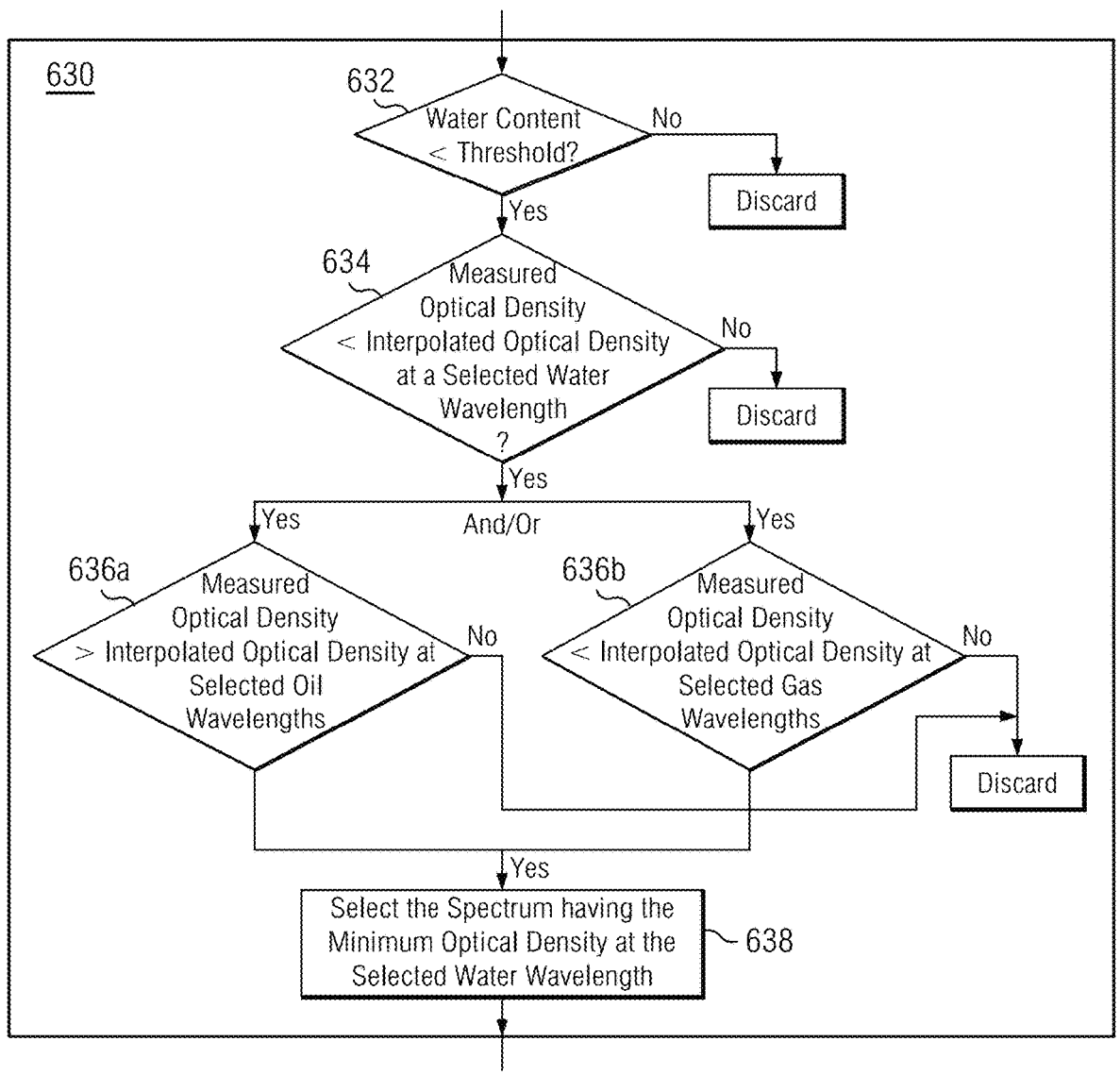
FIG. 11 depicts a flow chart of optional additional selection criteria for selecting an oil spectrum.

FIG. 11 depicts a flow chart of example selection criteria 630 for selecting an oil spectrum. First, second, and third criteria 632, 634, and 636a may be substantially identical to criteria 532, 534, and 536 (FIG. 10) described above for obtaining a gas condensate spectrum. In other embodiments, the third criteria 636b may (alternatively or additionally) select spectra for which the measured optical density of a gas peak is less than the optical density of the local background (or of the shoulder of the oil peak). For example, the measured optical density at one or more wavelengths corresponding to the gas peak (or shoulders thereof) may be compared with linearly interpolated estimated optical densities at those wavelengths and the spectrum may be selected when the measured optical density (ies) are less than the estimated optical density (ies). In example embodiments, this third criterion 636b may be expressed mathematically, for example, as follows:

$$\Omega(t,1650)_{MEAS}<\Omega(t,1600,1650,1725)_{INT} \quad (23)$$

$$\Omega(t,1671)_{MEAS}<\Omega(t,1600,1671,1725)_{INT} \quad (24)$$

$$\Omega(t,1690)_{MEAS}<\Omega(t,1600,1690,1725)_{INT} \quad (25)$$

A fourth criterion 638 may then select the spectrum from the remaining spectra which exhibits the smallest optical density at a distinguished water wavelength (e.g., 1930 nm) as given, for example, in Eq. (19).

Figure 12:
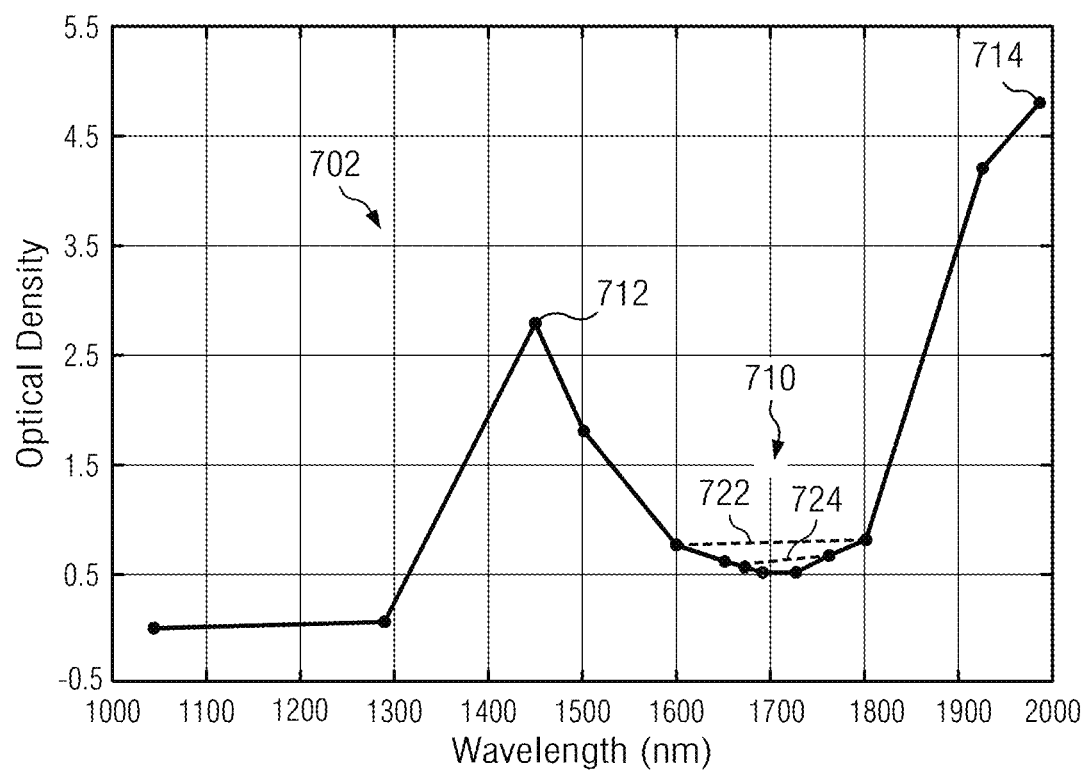
FIG. 12 depicts a portion of an optical density spectrum illustrating example criteria for selecting a water spectrum.

Turning now to FIG. 12 an example water spectrum is shown at 702 including first and second water peaks at 712 and 714. The region of the absent hydrocarbon peaks (gas, gas condensate, and oil) is generally depicted at 710. FIG. 12 further depicts the example criteria given in Eqs. (10)-(12) at 722 and Eqs. (13)-(14) at 724.

Figure 13:
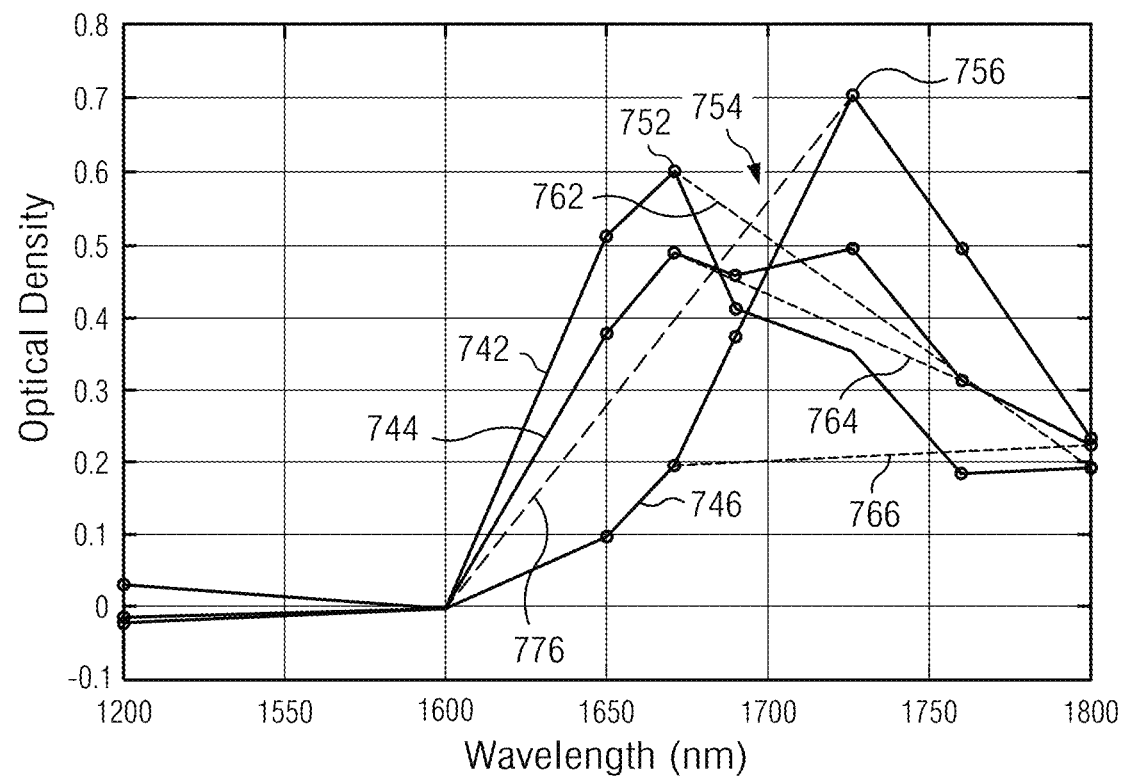
FIG. 13 depicts portion of optical density spectra illustrating example criteria for selecting gas, gas condensate, and oil spectra.

FIG. 13 depicts optical densities of portions of an example gas spectrum 742, an example gas condensate spectrum 744, and an example oil spectrum 746. In these example spectra, the gas peak is observed at 752, the broad gas condensate peak is observed generally at 754, and the oil peak is observed at 756. FIG. 13 further depicts example criteria given in Eqs. (16)-(18) at 762, Eqs. (20)-(22) at 764 and 766, and Eqs. (23)-(25) at 776.

Figure 14:
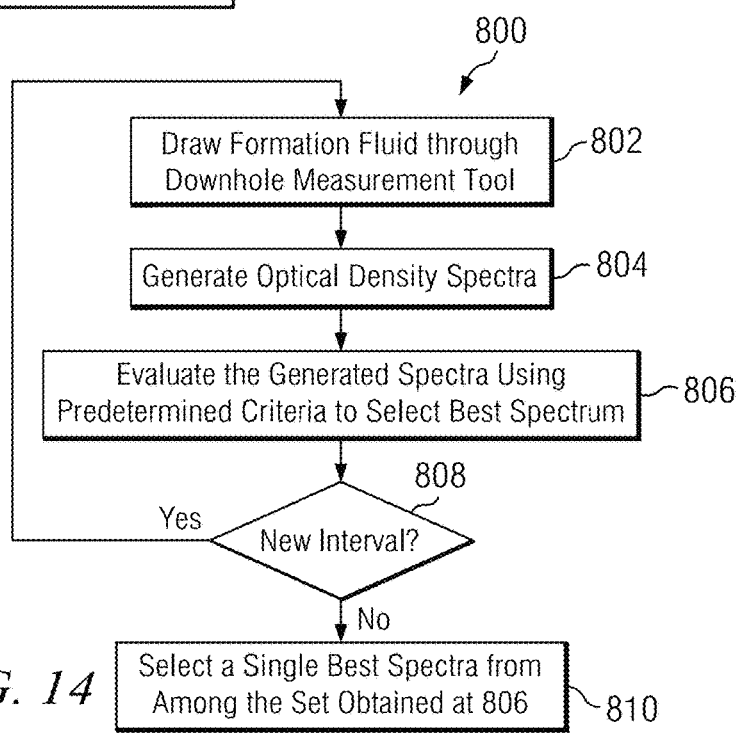
FIG. 14 depicts a flow chart of still another example method for making optical density measurements of a formation fluid.

FIG. 14 depicts a flow chart of still another example method 800 for making optical density measurements of a formation fluid. Method 800 may be particularly well suited for operations in which the formation fluid is mixed with or contaminated with oil from an oil based drilling fluid and there is free water present in the formation. Method 800 is similar to method 200 (FIG. 5) in that it includes generating optical density spectra at 804 while drawing formation fluid through a flowline in a fluid sampling and evaluation measurement tool at 802. The generated spectra are then evaluated with predetermined criteria at 806 to select a best spectrum (e.g., a single best gas, gas condensate, or oil spectrum as described above). The selection criteria at 806 may include any of the criteria described above with respect to FIGS. 6, 9, 10, and 11.

With continued reference to FIGS. 14, 804 and 806 may be repeated at a predetermined time interval (e.g., at 1, 5, or 10 minute intervals) or after a predetermined number of spectra have been generated at 804 to obtain a plurality of best spectra (a single best spectrum corresponding to each interval). After a certain number of time intervals or at the completion of the logging operation (e.g., at a particular station) 808, the set of best spectra may be further evaluated using additional criteria at 810 to obtain a single one of the best spectra.

It will be appreciated that drilling fluid contamination commonly decreases with time during a fluid sampling operation. Therefore, the additional criteria may include criteria that distinguish between formation fluids and synthetic oils (or other oils commonly used in drilling fluids). Two example criteria are disclosed herein. A first criterion recognizes that common drilling fluid oils are colorless. The first criterion may therefore select the spectrum having the maximum optical density (the most color) at a visible or near visible region of the spectrum (e.g., at a wavelength or wavelengths less than 1000 nm). In one example embodiment, the spectrum having a maximum optical density at 815 nm is selected, after a baseline shift has been performed. A second criterion may recognize that the synthetic oils in the drilling fluid do not generally include dissolved gases. The second criterion may therefore select the single spectrum from the set of best spectra having the highest ratio of the optical density of the gas peak to the optical density of the oil peak (e.g., $$\max_t \{\Omega(t, 1671)_{MEAS} - \Omega(t, 1600)_{MEAS}\}$$

$$\max_t \{[\Omega(t, 1671)_{MEAS} - \Omega(t, 1600)_{MEAS}]/[\Omega(t, 1725)_{MEAS} - \Omega(t, 1600)_{MEAS}]\}.$$

It will be understood that the present disclosure includes numerous embodiments. These embodiments include, but are not limited to, the following embodiments.

In a first embodiment, a method for evaluating a formation fluid comprises flowing formation fluid through a flowline in a downhole fluid sampling and evaluation measurement tool deployed in a wellbore; making optical absorption measurements on the flowing formation fluid to generate a plurality of optical density spectra; selecting a spectrum from the plurality of generated spectra using predetermined selection criteria, the selection criteria based on optical density values at one or more selected wavelengths in the generated spectra; and estimating a fluid property of the formation fluid from the selected spectrum.

A second embodiment may include the first embodiment, wherein the fluid property comprises at least one of a composition, a gas-oil ratio, a formation volume factor, a density, a compressibility, a saturation pressure, and an asphaltene content.

A third embodiment may include any one of the first through second embodiments, wherein the selected spectrum comprises a hydrocarbon spectrum and the selecting the at least one spectrum further comprises selecting spectra from the generated optical density spectra having an estimated water fraction less than a water fraction threshold to obtain first selected spectra; selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; and selecting the spectrum from the second selected spectra having a lowest optical density at the selected wavelength.

A fourth embodiment may include the third embodiment, wherein the spectra are selected from the first selected spectra when $$\Omega(t,\lambda 2)_{MEAS} < \Omega(t,\lambda 1,\lambda 2,\lambda 3)_{INT} + \epsilon_1$$

$$\Omega(t,\lambda 2)_{MEAS} < \Omega(t,\lambda 1,\lambda 2,\lambda 3)_{INT} - E_2$$

wherein $\Omega(t, \lambda 2)$ MEAS represents the measured optical density at a selected wavelength $\lambda 2$, and $\Omega(t, \lambda 1, \lambda 2, \lambda 3)_{INT}$ represents the estimated optical density at the selected wavelength obtained by interpolation using $\lambda 1$ and $\lambda 3$, $\epsilon_2 \sim 10\epsilon_1$ and $0.001 < \epsilon_1 < 0.01$ in optical density units.

A fifth embodiment may include any one of the first through fourth embodiments, wherein the selected spectrum comprises a gas spectrum and the selecting the at least one spectrum further comprises selecting spectra from the generated optical density spectra having an estimated water fraction less than a water fraction threshold to obtain first selected spectra; selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; selecting spectra from the second selected spectra for which the measured optical density of an oil peak is less than an optical density of a local background to obtain third selected spectra, the local background determined via interpolation; and selecting the spectrum from the third selected spectra having a lowest optical density at the selected wavelength.

A sixth embodiment may include any one of the first through fourth embodiments, wherein the selected spectrum comprises a gas condensate spectrum and the selecting the at least one spectrum further comprises selecting spectra from the generated optical density spectra having an estimated water fraction less than a water fraction threshold to obtain first selected spectra; selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; selecting spectra from the second selected spectra for which the measured optical density of an oil peak is greater than an optical density of a local background to obtain third selected spectra, the local background determined via interpolation; and selecting the spectrum from the third selected spectra having a lowest optical density at the selected wavelength.

A seventh embodiment may include any one of the first through fourth embodiments, wherein the selected spectrum comprises an oil spectrum and the selecting the at least one spectrum further comprises selecting spectra from the generated optical density spectra having an estimated water fraction less than a threshold to obtain first selected spectra; selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; selecting spectra from the second selected spectra for which the measured optical density of a gas peak is less than an optical density of a local background to obtain third selected spectra, the local background determined via interpolation; and selecting the spectrum from the third selected spectra having a lowest optical density at the selected wavelength.

An eighth embodiment may include any one of the first through second embodiments, wherein the selected spectrum comprises a water spectrum and the selecting the at least one spectrum further comprises selecting spectra from the generated optical density spectra having an estimated water fraction greater than a threshold to obtain first selected spectra; selecting spectra from the first selected spectra having a measured optical density at a selected wavelength that is less than or equal to an estimated optical density at the selected wavelength obtained by interpolation to obtain second selected spectra, wherein the selected wavelength is a wavelength of a hydrocarbon peak; and selecting the spectrum from the second selected spectra having a highest optical density of a water peak.

A ninth embodiment may include any one of the first through eighth embodiments, further comprising implementing the making optical absorption measurements and the selecting the spectrum for each of a plurality of time intervals to obtain a plurality of best spectra corresponding to the plurality of the time intervals; and selecting the best spectrum from among the plurality of best spectra, wherein the selected best spectrum has (i) the highest optical density at a preselected wavelength less than 1000 nm, (ii) the highest optical density of a preselected gas peak, or (iii) the highest ratio of the optical density of the preselected gas peak to an optical density of a preselected oil peak.

A tenth embodiment may include any one of the first through ninth embodiments, wherein the selecting the spectrum is performed automatically by a processor in the downhole fluid sampling and evaluation measurement tool.

In an eleventh embodiment, a downhole fluid sampling and evaluation measurement tool comprises a downhole tool body; a probe configured to engage a wellbore wall and draw formation fluid into the tool; an internal flowline in fluid communication with the probe; an optical measurement assembly configured to make optical absorption measurements of wellbore fluid in the internal flowline; and a controller configured to cause the tool to flow the formation fluid from the probe through the internal flowline; cause the optical measurement assembly to make a plurality of optical absorption measurements while flowing the wellbore fluid through the internal flowline to generate a plurality of optical density spectra; select a spectrum from the plurality of generated spectra using predetermined selection criteria, the selection criteria based on optical density values at one or more selected wavelengths in the generated spectra; and estimate a property of the formation fluid from the selected spectrum.

A twelfth embodiment may include the eleventh embodiment, wherein the downhole fluid sampling and evaluation measurement tool is a logging while drilling tool; and the controller is configured to cause the tool to flow the formation fluid and cause the optical measurement assembly to make the plurality of optical absorption measurements during a non-drilling interval.

A thirteenth embodiment may include any one of the eleventh through twelfth embodiments, wherein the selected spectrum comprises a hydrocarbon spectrum and the select a spectrum from the plurality of generated spectra further comprises select spectra from the generated optical density spectra having an estimated water fraction less than a water fraction threshold to obtain first selected spectra; select spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; and select the spectrum from the second selected spectra having a lowest optical density at the selected wavelength.

A fourteenth embodiment may include any one of the eleventh through thirteenth embodiments, wherein the selected spectrum comprises an oil spectrum and the select a spectrum from the plurality of generated spectra further comprises select spectra from the generated optical density spectra having an estimated water fraction less than a threshold to obtain first selected spectra; select spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; select spectra from the second selected spectra for which the measured optical density of a gas peak is less than an optical density of a local background to obtain third selected spectra, the local background determined via interpolation; and select the spectrum from the third selected spectra having a lowest optical density at the selected wavelength.

A fifteenth embodiment may include any one of the eleventh through fourteenth embodiments, wherein the controller is further configured to cause the optical measurement assembly to make a plurality of optical absorption measurements and the selecting the spectrum for each of a plurality of time intervals to obtain a plurality of best spectra corresponding to the plurality of the time intervals; and select the best spectrum from among the plurality of best spectra, wherein the selected best spectrum has (i) the highest optical density at a preselected wavelength less than 1000 nm, (ii) the highest optical density of a preselected gas peak, or (iii) the highest ratio of the optical density of the preselected gas peak to an optical density of a preselected oil peak.

In a sixteenth embodiment a method for evaluating a formation fluid comprises flowing formation fluid through a flowline in a downhole fluid sampling and evaluation measurement tool deployed in a drill string in a wellbore; making optical absorption measurements on the flowing formation fluid to generate a plurality of optical density spectra; selecting spectra from the generated optical density spectra having an estimated water fraction less than a water fraction threshold to obtain first selected spectra; selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; selecting at least one of a gas spectrum, a gas condensate spectrum, and an oil spectrum from the second selected spectra; and estimating a property of the formation fluid from the at least one of a gas spectrum, a gas condensate spectrum, and an oil spectrum.

A seventeenth embodiment may include the sixteenth embodiment, wherein the selecting at least one of a gas spectrum, a gas condensate spectrum, and an oil spectrum comprises selecting a gas spectrum and the selecting further comprises selecting spectra from the second selected spectra for which the measured optical density of an oil peak is less than an optical density of a local background to obtain third selected spectra, the local background determined via interpolation; and selecting the spectrum from the third selected spectra having a lowest optical density of water peak.

An eighteenth embodiments may include any one of the sixteenth through seventeenth embodiments, wherein the selecting at least one of a gas spectrum, a gas condensate spectrum, and an oil spectrum comprises selecting a gas condensate spectrum and the selecting further comprises selecting spectra from the second selected spectra for which the measured optical density of an oil peak is greater than an optical density of a local background to obtain third selected spectra, the local background determined via interpolation; and selecting the spectrum from the third selected spectra having a lowest optical density of a water peak.

A nineteenth embodiment may include any one of the sixteenth through eighteenth embodiments, wherein the selecting at least one of a gas spectrum, a gas condensate spectrum, and an oil spectrum comprises selecting an oil spectrum and the selecting further comprises selecting spectra from the second selected spectra for which the measured optical density of a gas peak is less than an optical density of a local background to obtain third selected spectra, the local background determined via interpolation; and selecting the spectrum from the third selected spectra having a lowest optical density of a water peak.

A twentieth embodiment may include any one of the sixteenth through nineteenth embodiments, wherein the flowing formation fluid through the flowline and the making optical absorption measurements on the flowing formation fluid are performed during a non-drilling interval; and the selecting and the estimating are performed automatically by a processor in the downhole fluid sampling and evaluation measurement tool.

Although extraction of hydrocarbon and/or water optical spectra has been described in detail, it should be understood that various changes, substitutions and alternations can be made herein without departing from the spirit and scope of the disclosure as defined by the appended claims.

The invention claimed is:

1. A method for evaluating a formation fluid, the method comprising:
flowing formation fluid through a flowline in a downhole fluid sampling and evaluation measurement tool deployed in a wellbore;
making optical absorption measurements on the flowing formation fluid to generate a plurality of optical density spectra;
selecting at least one spectrum from the plurality of generated spectra using predetermined selection criteria, the selection criteria based on optical density values at one or more selected wavelengths in the generated spectra; and
estimating a fluid property of the formation fluid from the selected spectrum;
wherein the selected spectrum comprises a hydrocarbon spectrum and the selecting the at least one spectrum further comprises:
selecting spectra from the generated optical density spectra having an estimated water fraction less than a water fraction threshold to obtain first selected spectra;
selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm; and
selecting the spectrum from the second selected spectra having a lowest optical density at the selected wavelength; and
wherein the spectra are selected from the first selected spectra when $$[(\Omega(t,\lambda 2)]\_MEAS < [(\Omega(t,\lambda 1,\lambda 2,\lambda 3)]\_INT + \epsilon\_1$$

$$[(\Omega(t,\lambda 2)]\_MEAS < [(\Omega(t,\lambda 1,\lambda 2,\lambda 3)]\_INT - \epsilon\_2$$

wherein $[(\Omega(t,\lambda 2)]\_MEAS$ represents the measured optical density at a selected wavelength $\lambda 2$, and $[(\Omega(t,\lambda 1,\lambda 2,\lambda 3)]\_INT$ represents the estimated optical density at the selected wavelength obtained by interpolation using $\lambda 1$ and $\lambda 3$, $\epsilon\_2 \sim 10\epsilon\_1$ and $0.001 < \epsilon\_1 < 0.01$ in optical density units.

2. The method of claim 1, wherein the fluid property comprises at least one of a composition, a gas-oil ratio, a formation volume factor, a density, a compressibility, a saturation pressure, and an asphaltene content.

3. The method of claim 1, wherein the selected spectrum comprises a gas spectrum and the selecting the at least one spectrum further comprises:
selecting spectra from the generated optical density spectra having an estimated water fraction less than a water fraction threshold to obtain first selected spectra;
selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm;
selecting spectra from the second selected spectra for which the measured optical density of an oil peak is less than an optical density of a local background to obtain third selected spectra, the local background determined via interpolation; and selecting the spectrum from the third selected spectra having a lowest optical density at the selected wavelength.

4. The method of claim 1, wherein the selected spectrum comprises a gas condensate spectrum and the selecting the at least one spectrum further comprises:

selecting spectra from the generated optical density spectra having an estimated water fraction less than a water fraction threshold to obtain first selected spectra;

selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm;

selecting spectra from the second selected spectra for which the measured optical density of an oil peak is greater than an optical density of a local background to obtain third selected spectra, the local background determined via interpolation; and selecting the spectrum from the third selected spectra having a lowest optical density at the selected wavelength.

5. The method of claim 1, wherein the selected spectrum comprises an oil spectrum and the selecting the at least one spectrum further comprises:

selecting spectra from the generated optical density spectra having an estimated water fraction less than a threshold to obtain first selected spectra;

selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm;

selecting spectra from the second selected spectra for which the measured optical density of a gas peak is less than an optical density of a local background to obtain third selected spectra, the local background determined via interpolation; and selecting the spectrum from the third selected spectra having a lowest optical density at the selected wavelength.

6. The method of claim 1, wherein the selected spectrum comprises a water spectrum and the selecting the at least one spectrum further comprises:

selecting spectra from the generated optical density spectra having an estimated water fraction greater than a threshold to obtain first selected spectra;

selecting spectra from the first selected spectra having a measured optical density at a selected wavelength that is less than or equal to an estimated optical density at the selected wavelength obtained by interpolation to obtain second selected spectra, wherein the selected wavelength is a wavelength of a hydrocarbon peak; and selecting the spectrum from the second selected spectra having a highest optical density of a water peak.

7. The method of claim 1, further comprising:

implementing the making optical absorption measurements and the selecting the spectrum for each of a plurality of time intervals to obtain a plurality of best spectra corresponding to the plurality of the time intervals; and selecting the best spectrum from among the plurality of best spectra, wherein the selected best spectrum has (i) the highest optical density at a preselected wavelength less than 1000 nm, (ii) the highest optical density of a preselected gas peak, or (iii) the highest ratio of the optical density of the preselected gas peak to an optical density of a preselected oil peak.

8. The method of claim 1, wherein the selecting the spectrum is performed automatically by a processor in the downhole fluid sampling and evaluation measurement tool.

9. A downhole fluid sampling and evaluation measurement tool comprising:

a downhole tool body;

a probe configured to engage a wellbore wall and draw formation fluid into the tool;

an internal flowline in fluid communication with the probe;

an optical measurement assembly configured to make optical absorption measurements of wellbore fluid in the internal flowline; and a controller configured to:

cause the tool to flow the formation fluid from the probe through the internal flowline;

cause the optical measurement assembly to make a plurality of optical absorption measurements while flowing the wellbore fluid through the internal flowline to generate a plurality of optical density spectra;

select a spectrum from the plurality of generated spectra using predetermined selection criteria, the selection criteria based on optical density values at one or more selected wavelengths in the generated spectra; and estimate a property of the formation fluid from the selected spectrum;

wherein the selected spectrum comprises an oil spectrum and the select the spectrum from the plurality of generated spectra further comprises:

select spectra from the generated optical density spectra having an estimated water fraction less than a threshold to obtain first selected spectra;

select spectra from the first selected spectra having a measured optical density at a selected wavelength that is less than an estimated optical density at the selected wavelength obtained by interpolation to obtain second selected spectra, wherein the selected wavelength is between 1800 nm and 2000 nm;

select spectra from the second selected spectra for which the measured optical density of a gas peak is less than an optical density of a local background to obtain third selected spectra, the local background determined via interpolation; and select the spectrum from the third selected spectra having a lowest optical density at the selected wavelength.

10. The downhole tool of claim 9, wherein:

the downhole fluid sampling and evaluation measurement tool is a logging while drilling tool; and the controller is configured to cause the tool to flow the formation fluid and cause the optical measurement assembly to make the plurality of optical absorption measurements during a non-drilling interval.

11. The downhole tool of claim 9, wherein the controller is further configured to:

cause the optical measurement assembly to make a plurality of optical absorption measurements and the selecting the spectrum for each of a plurality of time intervals to obtain a plurality of best spectra corresponding to the plurality of the time intervals; and select the best spectrum from among the plurality of best spectra, wherein the selected best spectrum has (i) the highest optical density at a preselected wavelength less than 1000 nm, (ii) the highest optical density of a preselected gas peak, or (iii) the highest ratio of the optical density of the preselected gas peak to an optical density of a preselected oil peak.

12. A method for evaluating a formation fluid, the method comprising:

flowing formation fluid through a flowline in a downhole fluid sampling and evaluation measurement tool deployed in a drill string in a wellbore;

making optical absorption measurements on the flowing formation fluid to generate a plurality of optical density spectra;

selecting spectra from the generated optical density spectra having an estimated water fraction less than a water fraction threshold to obtain first selected spectra;

selecting spectra from the first selected spectra having a measured optical density at a selected wavelength that is less than an estimated optical density at the selected wavelength obtained by interpolation to obtain second selected spectra, wherein the selected wavelength is between 1800 nm and 2000 nm;

selecting at least one of a gas spectrum, a gas condensate spectrum, and an oil spectrum from the second selected spectra, wherein (a) if the gas spectrum is selected, further comprising:
  selecting spectra from the second selected spectra for which the measured optical density of an oil peak is less than an optical density of a local background to obtain third selected spectra, the local background determined via interpolation; and
  selecting the spectrum from the third selected spectra having a lowest optical density of a water peak;

(b) if the gas condensate spectrum is selected, further comprising:
  selecting spectra from the second selected spectra for which the measured optical density of an oil peak is greater than an optical density of a local background to obtain third selected spectra, the local background determined via interpolation; and
  selecting the spectrum from the third selected spectra having a lowest optical density of a water peak;

(c) if the oil spectrum is selected, further comprising:
  selecting spectra from the second selected spectra for which the measured optical density of a gas peak is less than an optical density of a local background to obtain third selected spectra, the local background determined via interpolation; and
  selecting the spectrum from the third selected spectra having a lowest optical density of a water peak; and estimating a property of the formation fluid from the at least one of a gas spectrum, a gas condensate spectrum, and an oil spectrum.

13. The method of claim 12, wherein:

the flowing formation fluid through the flowline and the making optical absorption measurements on the flowing formation fluid are performed during a non-drilling interval; and the selecting and the estimating are performed automatically by a processor in the downhole fluid sampling and evaluation measurement tool.

* * * * *